United States Patent [19]

Luheshi et al.

[11] Patent Number: 5,086,170
[45] Date of Patent: Feb. 4, 1992

[54] PROCESS FOR THE PREPARATION OF AZABICYCLO COMPOUNDS

[75] Inventors: Abdul B. N. Luheshi, Hull; Robert K. Smalley, Urmston; Peter D. Kennewell, Okus; Robert Westwood, Kingston Bagpuize, all of Great Britain

[73] Assignee: Roussel Uclaf, Paris, France

[21] Appl. No.: 633,289

[22] Filed: Dec. 24, 1990

Related U.S. Application Data

[62] Division of Ser. No. 465,031, Jan. 16, 1990.

[30] Foreign Application Priority Data

Jan. 16, 1989 [GB] United Kingdom ............... 8900863

[51] Int. Cl.⁵ ............................................. C07D 487/04
[52] U.S. Cl. .................................... 540/303; 540/310; 546/113; 546/115; 548/453; 548/455
[58] Field of Search ..................... 540/303, 304, 310; 546/113, 115; 548/453, 455

[56] References Cited

U.S. PATENT DOCUMENTS 4,272,439 6/1981 Gingaly et al. ..................... 540/303
4,576,939 3/1986 Ross et al. ........................ 540/303

Primary Examiner—Nicholas S. Rizzo
Attorney, Agent, or Firm—Bierman and Muserlian

[57] ABSTRACT

A compound selected from the group consisting of a compound of the formula

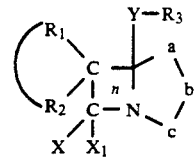

wherein $R_1$ and $R_2$ are individually selected from the group consisting of hydrogen, alkyl and hydroxyalkyl of 1 to 5 carbon atoms and amino, n is an integer from 1 to 3, X and $X_1$ are individually selected from the group consisting of hydrogen and alkyl of 1 to 3 carbon atoms or taken together with the carbon atom to which they are attached are

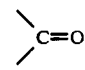

Y is —O— or —S—, $R_3$ is alkyl of 1 to 3 carbon atoms or aryl of 6 to 8 carbon atoms,

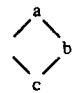

is selected from the group consisting of

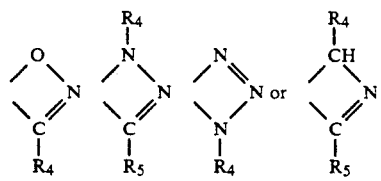

$R_4$ and $R_5$ are individually aryl unsubstituted or substituted with at least one member of the group consisting of halogen, —$NO_2$ and alkyl and alkoxy of 1 to 3 carbon atoms and non-toxic, pharmaceutically acceptable salts thereof with acids and bases having cyclooxygenase inhibiting and antibiotic acitvity.

5 Claims, No Drawings

PROCESS FOR THE PREPARATION OF AZABICYCLO COMPOUNDS

PRIOR APPLICATION

This application is a division of U.S. patent application Ser. No. 465,031 filed Jan. 16, 1990.

OBJECTS OF THE INVENTION

It is an object of the invention to provide the novel compounds of formula I and their salts and a novel process for their preparation.

It is another object of the invention to provide novel antibacterial compositions and compositions for inhibiting cyclooxygenase and a novel method of inducing cyclooxygenase inhibiting and antibacterial activity in warm-blooded animals.

These and other objects and advantages of the invention will become obvious from the following detailed description.

THE INVENTION

The novel compounds of the invention are compounds selected from the group consisting of a compound of the formula

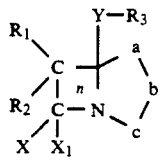

wherein $R_1$ and $R_2$ are individually selected from the group consisting of hydrogen, alkyl and hydroxyalkyl of 1 to 5 carbon atoms and amino, n is an integer from 1 to 3, X and $X_1$ are individually selected from the group consisting of hydrogen and alkyl of 1 to 3 carbon atoms or taken together with the carbon atom to which they are attached are

Y is —O— or —S—, $R_3$ is alkyl of 1 to 3 carbon atoms or aryl of 6 to 8 carbon atoms,

is selected from the group consisting of

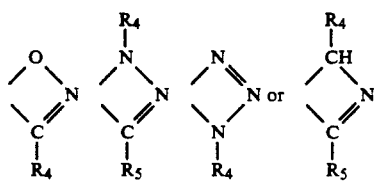

$R_4$ and $R_5$ are individually aryl unsubstituted or substituted with at least one member of the group consisting of halogen, —$NO_2$ and alkyl and alkoxy of 1 to 3 carbon atoms and non-toxic, pharmaceutically acceptable salts thereof with acids and base.

Examples of alkyl of 1 to 5 carbon atoms are methyl, ethyl, propyl, isopropyl or butyl and examples of hydroxyalkyl of 1 to 5 carbon atoms are hydroxymethyl, hydroxyethyl, hydroxypropyl or hydroxybutyl. Examples of alkyl of 1 to 3 carbon atoms are methyl, ethyl, propyl or isopropyl. Examples of aryl of 6 to 8 carbon atoms are phenyl and examples of halogen are fluorine, chlorine or bromine. Examples of alkoxy of 1 to 3 carbon atoms are methoxy, ethoxy, propoxy or isopropoxy.

Examples of acids to form non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartric acid, citric acid, oxalic acid glyoxylic acid and aspartic acid, and alkanesulfonic acids such as methanesulfonic acid and arylsulfonic acids such as benzene-sulfonic acid.

The scope of the invention also extends to base addition salts of compounds of formula I.

Among the preferred compounds of formula I are those wherein $R_1$ and $R_2$ are individually hydrogen, —$NH_2$, methyl or methoxy, those wherein X and $X_1$ are individually hydrogen or methyl or together are

those wherein $R_3$ is methyl or ethyl and their non-toxic, pharmaceutically acceptable salts. More preferably, $R_1$, $R_2$, X and $X_1$ are methyl, $R_3$ is ethyl and $R_4$ and $R_5$ are individually phenyl optionally substituted with $CH_3O$— or —$NH_2$ and n is 1 or 2.

Specific preferred compounds of formula I are:
3-(p-methoxyphenyl)-5,5,6,6-tetramethyl-7-ethoxy-1-oxa-2,4,6 diazabicyclo[3.2.0]hept-2-ene;
3-phenyl-5,5,6,6-tetramethyl-7-ethoxy-1-oxa-2,4-diazabicyclo [3.2.0]hept-2-ene;
3-(o-nitrophenyl)-5,5,6,6-tetramethyl-7-ethoxy-1-oxa-2,4-diazabicyclo[3.2.0]hept-2-ene;
3-(p-methoxyphenyl)-5,5,6,6-tetramethyl-7-ethylthio-1-oxa-2,4-diazabicyclo[3.2.0]hept-2-ene;
3-phenyl-5,5,6,6-tetramethyl-7-ethylthio-1-oxa-2,4-diazabicyclo[3.2.0]hept-2-ene;
3-(o-nitrophenyl)-5,5,6,6-tetramethyl-7-ethylthio-1-oxa-2,4-diazabicyclo[3.2.0]hept-2-ene;
7-ethoxy-1-(p-nitrophenyl)-3-phenyl-5,5,6,6-tetramethyl-1,2,4-triazabicyclo[3.2.0]hept-2-ene;
7-ethylthio-1-(p-nitrophenyl)-3-phenyl-5,5,6,6-tetramethyl-1,2,4-triazabicyclo[3.2.0]hept-2-ene;
7-ethoxy-3-phenyl-1-(p-nitrophenyl)-5,5,6,6-tetramethyl-2,4-diazabicyclo[3.2.0]hept-2-ene; and
7-ethylthio-3-phenyl-1-(p-nitrophenyl)-5,5,6,6-tetramethyl-2,4-diazabicyclo[3.2.0]hept-2-ene;
and salts thereof.

The novel process of the invention for the preparation of a compound of formula I comprises effecting a cycloaddition reaction between a compound of the formula

wherein

is as defined above and a compound of the formula

III

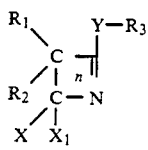

wherein $R_1$, $R_2$, n, X, $X_1$, Y and $R_3$ are as defined above.

The cycloaddition reaction between the compound of formula II and the compound of formula III may be conveniently effected in an apolar organic solvent such as benzene in the presence of an amine such as triethylamine.

When it is desired to prepare a compound of formula I in which

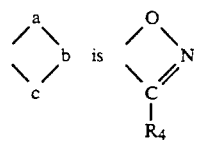

the compound of formula II used is a compound of the formula

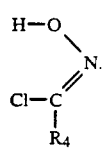

When it is desired to prepare a compound of formula I in which

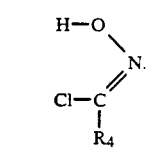

the compound of formula II used is a compound of the formula

II

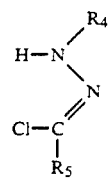

When it is desired to prepare a compound of formula I in which

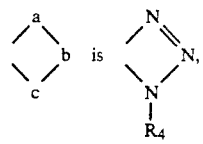

the compound of formula II used is a compound of the formula

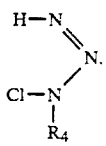

When it is desired to prepare a compound of formula I in which

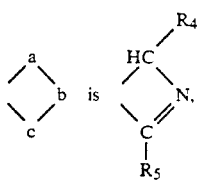

the compound of formula II used is a compound of the formula

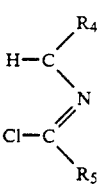

Some of the compounds of formula III can be prepared, for example, by a process analogous to that described in German patent application OLS-1,770,556. Some of the compounds of formula III are new and can be prepared, for example, according to the following scheme:

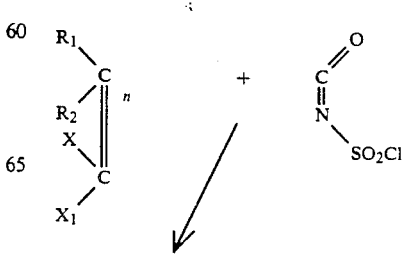

-continued

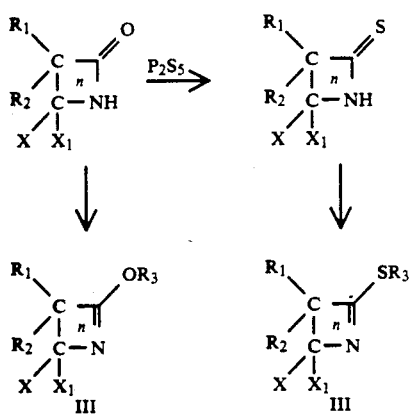

The compounds of formula II can be prepared by conventional methods, for example, as described in R. Huisgen, Angewandte Chem. (1963) Vol. 2, 565).

Compounds of formula I initially obtained by the above processes may, if desired, subsequently be converted into salts thereof. The addition salts of the compounds of formula I can advantageously be prepared by reacting in approximately stoichiometric quantities an inorganic or organic acid, or an approprate base with the compound of formula I. The salts can, if desired, be prepared without first isolating the compounds of formula I themselves.

The novel compositions of the invention for inhibiting cyclooxygenase (TX $B_2$ and 5-HHT) and to combat bacterial infections are comprised of an effective amount of at least one compound of formula I and its salts to combat bacteria and inhibit cyclooxygenase and an inert pharmaceutical carrier. The compositions may be in the form of tablets, dragees, capsules, granules, suppositories, syrups, aerosols and injectable solutions or emulsions.

Examples of suitable excipients are talc, gum arabic, lactose, starch, magnesium stearate, cocoa butter, aqueous or non-aqueous vehicles, animal or vegetable fats, paraffin derivatives, glycols, various wetting, dispersing or emulsifying agents and preservatives.

The compositions are useful for the treatment of inflammatory diseases, illnesses of the immuno-regulatory system and syndromes concerning the leucotrienes as well as the treatment of illnesses caused by gram-positive and gram-negative bacteria.

The novel method of the invention for inducing antibacterial or cyclooxygenase inhibiting activity in warm-blooded animals, including humans, comprises administering to warm-blooded animals on antibacterial or cyclooxygenase inhibiting activity of at least one compound of formula I and their non-toxic, pharmaceutically acceptable salts. The compounds may be administered orally, rectally or parentally. The usual daily dose is 0.0033 to 0.133 mg/kg depending on the condition treated, the method of administration and the specific compound.

In the following examples there are described several preferred embodiments to illustrate the invention. However, it should be understood that the invention is not intended to be limited to the specific embodiments.

EXAMPLE 1

3-(p-methoxyphenyl)-5,5,6,6-tetramethyl-7-ethoxy-1-oxa-2,4-diazabicyclo[3.2.0]hept-2-ene;

To a stirred solution of 200 mg (1.29 mmol) of 2-ethoxy-3,3,4,4-tetramethyl-1-azetine and 240 mg (1.29 mmol) of the hydroximoyl chloride in 20 ml of dry benzene under an inert atmosphere. 0.17 ml (1.29 mmol) of triethylamine were added dropwise and the mixture was stirred at room temperature for 2 hours. The precipitated triethylammonium hydrochloride was filtered off and was washed with dichloromethane. The filtrate and washings were combined and the solvent was removed under vacuum. The residue was subjected to column chromatography to obtain the pure product with a melting point of 107°–109° C. (light petrolium).

NMR Spectrum: epsilon 0.96 (s,3H); epsilon 1.19 (m,9H); epsilon 1.35 (s,3H); epsilon 3.22 (dq.2H); epsilon 3.88 (s,3H); epsilon 6.92 (d,2H); epsilon 7.53 (d,2H.

Analysis: $C_{17}H_{24}N_2O_3$. Calculated: %C 67.08; %H 7.95; %N 9.20. Found: 66.80; 7.93; 9.12.

2-ethoxy-3,3,4,4-tetramethyl-1-azetine

Step A

1-Chlorosulfonyl-3,3,4,4-tetramethyl-azetidinone

To a stirred solution of 0.06 mol CSI (chlorosulfonyl isocyanate in dry ether under nitrogen, 0.06 mol of 2,3-dimethyl-but-2-ene was added dropwise at a temperature of 30° to 35° C. The reaction mixture was stirred for a further 1 hour while it was cooled to room temperature. The solution was then cooled in a salt-ice bath and the product which crystallized out as white solid was filtered off and carried through to the next step.

STEP B:

Hydrolysis of N-chlorosulfonyl tetramethyl azetidinone

A solution of 10 g of the above azetidinone in ether was added dropwise to a thoroughly stirred mixture of 20 ml of water, 25 g of ice, 12 g of $NaHCO_3$ and 8 g of $Na_2SO_3.7H_2O$ at a temperature of 0°–5° C. After the addition was complete, the mixture was stirred for a further 1 hour at 0°–5° C. and the inorganic solids were then filtered off and the organic phase separated out. The aqueous phase was extracted twice with $CH_2Cl_2$ and the combined organic extracts were dried over $MgSO_4$ and the solvent removed under vacuo to obtain the product as a white solid.

NMR; 1.18 (s, 6H, 2Me); 1.26 (s, 6H, 2Me); 6.95 (broad s, 1H, NH).

STEP C 2-ethoxy-3,3,4,4-tetramethyl-1-azetine

To a solution of 60 ml (1M) of triethyloxonium tetraflouroborate in dichloromethane was added 5 g (0.039 mol) of tetramethylazetidinone in 10 ml of dry $CH_2Cl_2$ under an inert atmosphere. The reaction mixture was stirred for 1 hour at room temperature and then was refluxed for 1 hour. After cooling, the reaction mixture was added dropwise to 20 ml of a 50% $K_2CO_3$ solution at −10° C. and the mixture was diluted with 20 ml of $CH_2Cl_2$ and then filtered. The organic phase was separated out and immediately dried over $MgSO_4$. After filtration, the solvent was stripped off under vacuum and the residue was distilled at 78° to 80° C./50 mmHg to obtain the product as a colorless oil.

Spectral Data

NMR: epsilon 1.12 (s,6H); epsilon 1.18 (s,6H); epsilon 1.26 (t,3H); epsilon 4.12 (q,2H).
IR: 1630 cm$^{-1}$ (C=N).

EXAMPLE 2

3-phenyl-5,5,6,6-tetramethyl-7-ethoxy-1-oxa-2,4-diazabicyclo [3.2.0]hept-2-ene

Using the procedure of Example 1, the corresponding compound of formula II was reacted to obtain a 60% yield of 3-phenyl-5,5,6,6-tetramethyl-7-ethoxy-1-oxa-2,4-diazabicyclo [3.2.0]hept-2-ene melting at 106° to 108° C.

EXAMPLE 3

3-(o-nitrophenyl)-5,5,6,6-tetramethyl-7-ethoxy-1-oxa-2,4-diazabicyclo[3.2.0]hept-2-ene Using the procedure of Example 1, the corresponding compound of formula II was reacted to obtain a 34% yield of the 3-(o-nitrophenyl)-5,5,6,6-tetramethyl-7-ethoxy-1-oxa-2,4-diazabicyclo[3.2.0hept-2-ene melting at 103° to 104° C.

EXAMPLE 4

3-(p-methoxyphenyl)-5,5,6,6-tetramethyl-7-ethylthio-1-oxa-2,4-diazabicyclo[3.2.0]hept-2-ene To a stirred solution of 200 mg (1.17 mmol) of 2-ethylthio-3,3,4,4-tetramethyl-1-azetine and 220 mg (1.17 mmol) of the hydroximoyl chloride in 20 ml of dry benzene under an inert atmosphere. 0.17 ml (1.3 mmol) of triethylamine was added dropwise and the mixture was stirred at room temperature for 2 hours. The precipitated triethylammonium hydrochloride was filtered off and washed with dichlormethane. The wash waters and filtrate were combined and the solvent removed under vacuum. The residue was subjected to column chromatography to obtain the pure product as a white crystalline solid melting at 106° to 108° C. (hexane).

NMR Spectrum: epsilon 1.0 (s, 3H); epsilon 1.12 (m, 9H); epsilon 1.44 (s, 3H); epsilon 2.55 (dq, 2H); epsilon 3.68 (s,3H); epsilon 6.93 (d,2H); epsilon 7.53 (d, 3H).

Analysis: $C_{17}H_{24}N_2O_2S$. Calculated: %C 63.75; %H 7.50; %N 8.75; %S 10.00. Found: 63.56; 7.52; 8.69; 9.94.

2-ethylthio-3,3,4,4-tetramethyl-1-azetin

STEP A 3,3,4,4-tetramethylazetidinthione

To a stirred solution of 1 g of the compound of Step B of Example 1 in 15 ml of dry THF, 1.59 g of Lawesson's reagent were added under nitrogen and the mixture was stirred for 20 minutes, then heated at 60° C. for 20 minutes. After cooling, the solvent was removed under vacuum and the residue was chromatographed (pet. ether: EtOAc 7:3) to obtain a 50 to 70% yield of the product as a white solid melting at 117° to 118° C.

NMR: 1.2 (s,6H,2Me); 1.32 (s,6H,2Me); 8.3 (broad s,1H,NH).

STEP B 2-ethylthio-3,3,4,4-tetramethyl-1-azetine

To a solution of 10.5 ml of triethyloxonium tetrafluoroborate as a 1M solution in $CH_2Cl_2$, a solution of 1 g (7 mmol) of tetramethylazetidinethione in 3 ml of dry $CH_2Cl_2$ was added under an inert atmosphere. The mixture was stirred at room temperature for 1 hour and then reflux for 1 hour. After cooling, it was added dropwise to 10 mol of a 50% $K_2CO_3$ solution at $-10°$ C. After filtration, the organic phase was separated out and immediately dried over $MgSO_4$. Filtration was followed by removal of the solvent under vacuum and the oily residue was subjected to flash silica chromatography (pet. ether : ethyl acetate ; 8:2) to obtain the product as a colorless oil.

NMR: epsilon 1.12 (s,6H); epsilon 1.22 (s,6H); epsilon 1.28 (t,3H); epsilon 2.99 (q,2H).
IR: 1640 cm$^{-1}$ (C=N).

EXAMPLE 5

3-phenyl-5,5,6,6-tetramethyl-7-ethylthio-1-oxa-2,4-diazabicyclo [3.2.0]hept-2-ene Using the procedure of Example 4, the corresponding compound of formula II was reacted to obtain a 62% yield of 3-phenyl-5,5,6,6-tetramethyl-7-ethylthio-1-oxa-2,4-diazabicyclo[3.2.0]hept-2-ene melting at 132° to 134° C.

EXAMPLE 6

3-(o-nitrophenyl)-5,5,6,6-tetramethyl-7-ethylthio-1-oxa-2,4-diazabicyclo[3.2.0]hept-2-ene Using the procedure of Example 4, the corresponding compound of formula II was reacted to obtain a 42% yield 3-(o-nitrophenyl)-5,5,6,6-tetramethyl-7-ethylthio-1-oxa-2,4-diazabicyclo[3.2.0]hept-2-ene melting at 90° to 91° C.

EXAMPLE 7

7-ethoxy-1-(p-nitrophenyl)-3-phenyl-5,5,6,6-tetramethyl-1,2,4-triazabicyclo[3.2.0]hept-2-ene To a stirred solution of 1.46 mmol of 3,3,4,4-tetramethyl-2-ethoxy-1-azetine and 1.75 mmol of chlorobenzaldehyde (p-nitrophenyl)-hydrazone in 20 ml of dry benzene under an atmosphere of dry nitrogen, 4 equv. of triethylamine were added dropwise and the mixture was heated at reflux and was followed by TLC. When the reaction was completed, the precipitated triethylene hydrochloride was filtered off and the solvent was removed under vacuum. The residue was then purified by trituration with pet. ether (Eb 60°/80° C.) to obtain an 87% yield of the product melting at 141° to 143° C. (crystallized from pet. ether 40/60).

α-chlorobenzaldehyde (p-nitrophenyl) hydrazone

STEP A

N-benzoyl-N'-(p-nitrophenyl) hydrazide

To a stirred solution of 0.014 mol of p-nitrophenyl hydrazine in 10 ml of pyridine, 2 g (0.014 mmol) of benzoyl chloride were added dropwise and the mixture was stirred for 20 minutes and then was poured into ice cold water and stirred until a solid precipitated out. The solid was filtered, washed with water and then dried at 100° C. and the hydrazide was crystallized from ethanol to obtain an 83% yield of N-Benzoyl-N'-(p-nitrophenyl) hydrazide melting at 190° to 192° C. (lit m.pt. 193° to 194° C.).

STEP B

α-chlorobenzaldehyde (p-nitrophenyl) hydrazone

An intimately ground mixture of 0.07 mol of the dry hydrazide and 0.07 mol of phosphorous pentachloride was dissolved in 50 ml of dry ether and the mixture was refluxed overnight. After cooling, a solution of 30 g of phenol in 50 ml of dry ether was added to the reaction mixture followed by 40 ml of methanol. When the exthormic reaction subsided, the solvent was reduced to half bulk, and the remainder was allowed to cool over several days in the refrigerator to obtain α-chlorohydrazone which crystallized as dark needles to obtain 79% yield of chlorobenzaldehyde (p-nitrophenyl) hydrazone melting at 188° to 190° (lit 189° to 191° C. R. Huisgen et al—Chem. Berichte (1964) Vol. 97 p. 1085).

EXAMPLE 8

7-ethylthio-1-(p-nitrophenyl)-3-phenyl-5,5,6,6-tetramethyl 1,2,4-triazobicyclo[3.2.0]hept-2-ene Using the method of Example 7, the corresponding 2-ethylthio-1-azetine was reacted to obtain an 88% yield of 7-ethylthio-1-(p-nitrophenyl)-3-phenyl-5,5,6,6-tetramethyl 1,2,4-triazobicyclo[3.2.0]hept-2-ene melting at 153° to 154° C.

EXAMPLE 9

7-ethoxy-3-phenyl-1-(p-nitrophenyl)-5,5,6,6-tetramethyl-2,4-diazobicyclo[3.2.0]hept-2-ene To a solution of 2.18 mmol of 3,3,4,4-tetramethyl-2-ethoxy-azotine and 2.18 mmol of imidoyl chloride in 20 ml of dry benzene under an atmosphere of dry nitrogen, 1.5 eqv. of triethylamine were added. After stirring for several hours at room temperature, a precipitate was gradually formed. When the reaction appeared complete, the precipitate was filtered off and the solvent was removed under vacuum to leave an oily residue which was purified by flash silica chromatography to obtain a 46% yield of the adduct as a crystalline solid melting at 165° to 167° C. (cryst from pet. ether 60/80).

N-(p-nitrobenzyl)-benzimidoyl chloride

A solution of 3.7 mmol of N-(p-nitrobenzyl)-benzamide in thionyl chloride was refluxed under an inert atmosphere for 30 minutes and after cooling, the excess thionyl chloride was removed under vacuum to leave a solid residue. The residue was crystallized from dry cyclohexane under dry nitrogen (Note: the subsequent filtration had to be done under dry nitrogen also to obtain an 85% yield of the purified imidoyl—chloride melting at 71° to 73° C. (Lit. m.pt. 73-4Huisgen et al— Loc. cit) which was used directly in the next step.

EXAMPLE 10

7-ethylthio-3-phenyl-1-(p-nitrophenyl)-5,5,6,6-tetramethyl-2,4-diazabicyclo[3.2.0]hept-2-ene Using the procedure of Example 9, the corresponding 2-ethylthio-1-azetine was reacted to obtain a 68% yield of 7-ethylthio-3-phenyl-1-(p-nitrophenyl)-5,5,6, 6-tetramethyl 2,4-diazabicyclo[3.2.0]hept-2-ene melting at 148° to 149° C.

EXAMPLE 11

7a-ethoxy-3-(4-methoxy phenyl)-5,6,7,7a-tetrahydropyrrolo[1,2-d][1,2,4]oxadiazol-5-one A mixture of 2.27 g (0.01 mmol) of 0-ethylsuccinimide [Matoba et al, Chem., Pharm. Bull, Vol. 22 (12), p. 2999-3001 (1974)] and 1.86 g (0.01 mol) of 4-methoxybenzohydroximinoyl chloride in 50 ml of dry benzene was stirred at room temperature under an atmosphere of dry nitrogen while 1.31 g (0.013 mol) of triethylamine were added dropwise. The resulting mixture was stirred at room temperature for 4 days and then the precipitated triethylammonium chloride was filtered off. The filtrate was evaporated and the residual brown oil was purified by flash chromatography (silica gel. 100 g; $CH_2Cl_2$) to obtain 0.49 g (18% yield) of the title compound as a white crystalline solid melting at 114° to 116° C. (crystallization from 40 to 60 ether-petroleum ether).

IR Spectrum $CHCl_3$ solution: 2980, 1750, 1610, 1365, 1250, 1100, 870 and 835 $cm^{-1}$;

NMR ($CDCl_3$); epsilon 1.23 (3H, t, J=7.2 Hz, —$CH_3$), 2.50-2.77 (3H,m $C_6$-H, 2×$C_7$-H, 3.00-3.06 (1H, q of AB doublet, $J_{H6H6'}$, 16.9 Hz, $J_{H6,H7}$ 11.6Hz, $H_{H6,}H_{7'}$, 8.5Hz, $C_6$-H), 3.35-3.61 (2H, q of AB quartet, $J_{AB}$8.9 Hz, $J_{AX}=J_{BX}$7.2Hz, —$OCH_2$); 3.85 (3H, s, —$OCH_3$); 6.95 and 7.79 (4H, $AB_q$, aromatic).

EXAMPLE 12

Tablets were prepared containing 100 mg of the compound of Example 1 or 4 and sufficient excipient of lactose, starch, talc and magnesium stearate for a final weight of 200 mg.

EXAMPLE 13

A preparation for injection was prepared with 500 mg of the compound of Example 1 and sterile aqueous excipient for a volume of 5 ml.

EXAMPLE 14

Capsules were prepared containing 250 mg of the compound of Example 5 and excipient qs. for a capsule of 400 mg. (excipient : talc, magnesium stearate, aerosil).

PHARMACOLOGICAL ACTIVITY

The compounds were tested for their activity as inhibitors of the synthesis of eicosanoids by guinea pig peritoneal neutrophils following the addition of [$^{14}$C]-arachidonic acid and calcium ionophore, using a modification of the method published by Harvey et al [J. Pharmacol. Methods, Vol. 9(2), p 147-155 (1983)]. The compounds of the invention selectively inhibit cyclooxygenase product (TX $B_2$ and 5-HHT) synthesis. Less potent effects are shown against 5-lipoxygenase product (5-HETE) synthesis. In these tests, compound 4 showed $IC_{50}$ (micromolar) of 5.0 (TXB$_2$), 6.3 (5-HHT) and >100 (5-HETE).

Various modifications of the compounds and methods of the invention may be made without departing from the spirit or scope thereof and it is to be understood that the invention is intended to be limited only as defined in the appended claims.

What is claimed is:

1. A process for the preparation of a compound selected from the group consisting of a compound of the formula

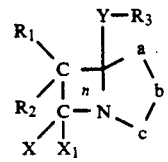

I wherein $R_1$ and $R_2$ are individually selected from the group consisting of hydrogen, alkyl and hydroxyalkyl of 1 to 5 carbon atoms and amino, n is an integer from 1 to 3, X and $X_1$ are individually selected from the group consisting of hydrogen and alkyl of 1 to 3 carbon atoms or taken together with the carbon atom to which they are attached are

Y is —O— or —S—, R₃ is alkyl of 1 to 3 carbon atoms or aryl of 6 to 8 carbon atoms,

is selected from the group consisting of

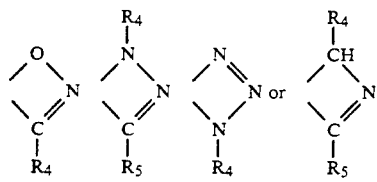

$R_4$ and $R_5$ are individually aryl unsubstituted or substituted with at least one member of the group consisting of halogen, —NO₂ and alkyl and alkoxy of 1 to 3 carbon atoms and non-toxic, pharmaceutically acceptable salts thereof with acids and bases comprising effecting a cyclo addition reaction between a compound of the formula

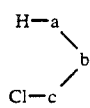

wherein

is as defined above and a compound of the formula

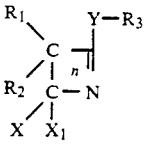

wherein $R_1$, $R_2$, n, X, $X_1$, Y and $R_3$ are as defined above to obtain the compound of formula I.

2. The process of claim 1 wherein the compound of formula II has the formula

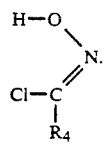

3. The process of claim 1 wherein the compound of formula II has the formula

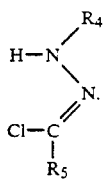

4. The process of claim 1 wherein the compound of formula II has the formula

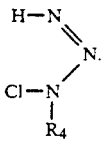

5. The process of claim 1 wherein the compound of formula II has the formula

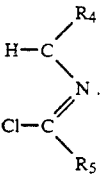

* * * * *

UNITED STATES PATENT AND TRADEMARK OFFICE
CERTIFICATE OF CORRECTION

PATENT NO. : 5,086,170

DATED : Feb. 4, 1992

INVENTOR(S) : ABDUL B.N. LUHESHI, ET AL

It is certified that error appears in the above-indentified patent and that said Letters Patent is hereby corrected as shown below:

| Col. | Claim | Line |
|------|-------|------|
| 10   | 1     | 60   |

"  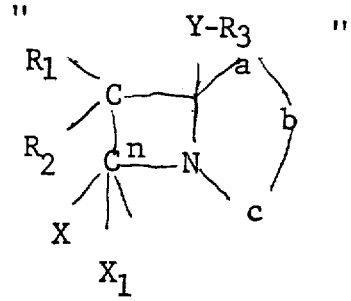  "

should be

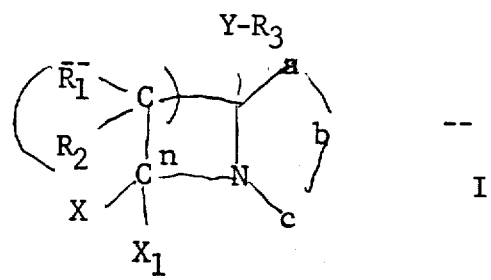    -- I

UNITED STATES PATENT AND TRADEMARK OFFICE
CERTIFICATE OF CORRECTION

PATENT NO. : 5,086,170
DATED : Feb. 4, 1992
INVENTOR(S) : ABDUL B.N. LUHESHI, ET AL

It is certified that error appears in the above-indentified patent and that said Letters Patent is hereby corrected as shown below:

Col. 12, Claim 1, line 5,

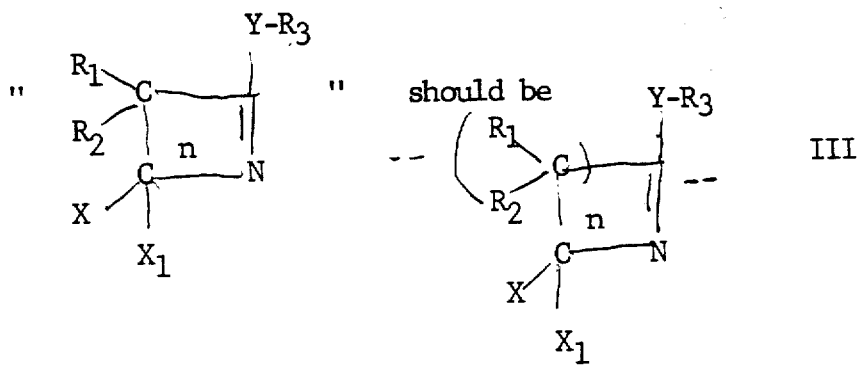

Signed and Sealed this

Eighth Day of June, 1993

Attest:

MICHAEL K. KIRK

Attesting Officer     Acting Commissioner of Patents and Trademarks